US010963488B2

(12) United States Patent
Muñoz-Jiménez et al.

(10) Patent No.: US 10,963,488 B2
(45) Date of Patent: Mar. 30, 2021

(54) SIMILARITY-COMPUTATION APPARATUS, A SIDE EFFECT DETERMINING APPARATUS AND A SYSTEM FOR CALCULATING SIMILARITIES BETWEEN DRUGS AND USING THE SIMILARITIES TO EXTRAPOLATE SIDE EFFECTS

(71) Applicant: FUJITSU LIMITED, Kawasaki (JP)

(72) Inventors: Emir Fernando Muñoz-Jiménez, Galway (IE); Ahmed Abdelrahman, Dublin (IE); Vit Nováček, Galway (IE); Pierre-Yves Vandenbussche, Galway (IE)

(73) Assignee: FUJITSU LIMITED, Kawasaki (JP)

( * ) Notice: Subject to any disclaimer, the term of this patent is extended or adjusted under 35 U.S.C. 154(b) by 399 days.

(21) Appl. No.: 15/087,902

(22) Filed: Mar. 31, 2016

(65) Prior Publication Data

US 2016/0321407 A1    Nov. 3, 2016

(30) Foreign Application Priority Data

Apr. 30, 2015   (GB) .................................. 1507501.3
Dec. 7, 2015    (EP) .................................... 15198304

(51) Int. Cl.
*G06F 16/28* (2019.01)
*G16H 10/20* (2018.01)
(Continued)

(52) U.S. Cl.
CPC ........... *G06F 16/285* (2019.01); *G16C 20/40* (2019.02); *G16H 10/20* (2018.01); *G16H 10/60* (2018.01); *G16H 70/40* (2018.01); *G16H 70/60* (2018.01)

(58) Field of Classification Search
CPC ............. G06F 19/326; G06F 17/30598; G06F 16/285; G16H 10/60; G16H 10/20; G16C 20/40
(Continued)

(56) References Cited

U.S. PATENT DOCUMENTS 6,789,091 B2    9/2004  Gogolak
7,979,373 B2    7/2011  Gogolak
(Continued)

OTHER PUBLICATIONS

Sharifullah Khan, Effective semantic search using thematic similarity, Oct. 22, 2013, Journal of King Saud University—Copmuter and Information Sciences (2014) 26, pp. 161-169.*
(Continued)

*Primary Examiner* — Robert A Sorey
*Assistant Examiner* — Kimberly A. Sass
(74) *Attorney, Agent, or Firm* — Westerman, Hattori, Daniels & Adrian, LLP

(57) ABSTRACT

A system for calculating similarities between drugs and using the similarities to extrapolate side effects of a specified drug comprising: a similarity-computation apparatus configured to use open data to compute similarities between drugs, with: a data integration module configured to obtain data related to a set of drugs from a plurality of open data sources and to integrate the data to generate RDF triples; an RDF module configured to store an RDF graph of the RDF triples: and a similarity calculation module configured to retrieve a list of all the drugs present in the RDF graph and to calculate the similarity of each drug with every other drug in the RDF graph, for storage in a similarity database; and a side effect determining apparatus configured to extrapolate side effects of a specified drug from open data related to the set of drugs, with: a connection to the similarity database; a user interface configured to allow a user to specify a drug from the set of drugs; a neighbours ranking module config- (Continued)

ured to use the drug similarities to obtain nearest neighbours of the specified drug in terms of the similarities; and a side effects propagation module configured to collect known side effects from the nearest neighbours and to combine and rank the side effects according to their co-occurrence among the neighbours.

10 Claims, 8 Drawing Sheets

(51) Int. Cl.
  *G16H 10/60* (2018.01)
  *G16C 20/40* (2019.01)
  *G16H 70/40* (2018.01)
  *G16H 70/60* (2018.01)
(58) Field of Classification Search
  USPC .................................................. 705/3
  See application file for complete search history.

(56) References Cited

U.S. PATENT DOCUMENTS

| 8,543,422 | B2 | 9/2013 | Maman et al. |
| 8,793,208 | B2* | 7/2014 | Rojahn ............. G06F 17/30734 706/50 |
| 2008/0201172 | A1* | 8/2008 | McNamar ............. G06Q 50/24 705/3 |
| 2011/0101099 | A1 | 5/2011 | Trajkovic et al. |
| 2011/0106807 | A1* | 5/2011 | Srihari ............. G06F 17/30604 707/739 |
| 2013/0144636 | A1 | 6/2013 | Pouliot et al. |
| 2013/0179375 | A1 | 7/2013 | Tatonetti et al. |
| 2013/0268290 | A1* | 10/2013 | Jackson ............. G06F 19/28 705/2 |
| 2014/0379630 | A1 | 12/2014 | Horvitz et al. |

OTHER PUBLICATIONS

Graham Klyne, Resource Description Framework (RDF): Concepts and Abstract Syntax, Feb. 10, 2004, W3C, pp. 1-18.*

Tomas Mikolov, Efficient Estimation of Word Representations in Vector Space, Sep. 7, 2013, Cornell University Library, pp. 1-12.*
Extended (Supplemental) European Search Report (EESR) dated May 5, 2016, issued in counterpart European Patent Application No. 15198304.6. (7 pages).
Christian Bizer; "The Emerging Web of Linked Data"; The Semantic Web, Sep./Oct. 2009; IEEE Intelligent Systems; http://www.computer.org/intelligent; pp. 87-92.
Egon L. Willighagen, et al.; "The ChEMBL database as linked open data"; Journal of Cheminformatics; 2013, vol. 5; No. 23; pp. 1-12.
Xiaoyan A. Qu, et al.; "Inferring novel disease indications for known drugs by semantically linking drug action and disease mechanism relationships"; BMC Bioinformatics; BioMed Central; 2009; vol. 10(Suppl 5):S4.
Egon L. Willighagen, et al.; "Linking Open Drug Data to Cheminformatics and Proteochemometrics"; Uppsala University, Department of Pharmaceutical Biosciences; 2010; http://www.farmbio.uu.se/.
Liat Perlman et al.; "Combining Drug and Gene Similarity Measures for Drug-Target Elucidation"; Research Articles; Journal of Computational Biology; The Blavatnik School of Computer Science and School of Medicine, Tel Aviv University; vol. 18; No. 2, (2011); pp. 133-145.
Linker et al., "Treatment costs associated with interventional cancer clinical trials conducted at a single UK institution over 2 years (2009-201 0)", British Journal of Cancer, 2013, 109, pp. 2051-2057.
Bates et al., "Incidence of Adverse Drug Events and Potential Adverse Drug Events", Original Contributions, JAMA, Jul. 5, 1995, vol. 274, No. 1 (6 pages).
Meymandpour et al., "Ranking Universities Using Linked Open Data", LDOW2013, May 14, 2013, Rio de Janeiro, Brazil (8 pages).
Examiner's Opinion dated Nov. 27, 2015, issued in counterpart of German Application No. GB1507501.3 (4 pages).
Xu et al., "Large-scale combining signals from both biomedical literature and the FDA Adverse Event Reporting System (FAERS) to improve post-marketing drug safety signal detection", BMC Bioinformatics, 2014, (10 pages).
Wang et al., "Exploring the associations between drug side-effects and therapeutic indications", Journal of Biomedical Informatics, 51, 2014 (9 pages).

* cited by examiner

SIMILARITY-COMPUTATION APPARATUS, A SIDE EFFECT DETERMINING APPARATUS AND A SYSTEM FOR CALCULATING SIMILARITIES BETWEEN DRUGS AND USING THE SIMILARITIES TO EXTRAPOLATE SIDE EFFECTS

The present invention relates to a method allowing early stage signalling of drug side effects using open data. The method can determine side effects potentially associated with drugs, by means of computing drug similarity based on intrinsic properties. The invention is in the field of Pharmacoinformatics and has applications throughout the world of medicine.

BACKGROUND OF THE INVENTION

Side effects are unintended or unwanted effects of using a drug (any substance (with the exception of food and water) that alters a body's function, for humans or animals) that occur along with the desired effects of the drug. Examples include agitation, headaches, wound infection and nausea. Pre-market drug trials and studies are often used to initially determine side effects associated with a drug. However, pre-market drug trials are, in general, expensive and risky. Despite such studies, numerous unknown side effects are reported after the market release of a drug (i.e. in a post-market period), which can, in many cases, cause substantial morbidity and even mortality. When such events occur, among other actions, the drug is removed from the market, which can hugely damage the image and reputation of a pharmaceutical company and cause legal issues. Thus, lower-cost systems to detect prematurely (i.e. in the early stage of drugs manufacture) drug side effects would help to minimise future costs, as well as avoiding risks to both pharmaceuticals and the general public.

To cope with the inconclusiveness of the pre-market clinical trials, side effects are globally monitored after the release of a drug by organisations such as the Food and Drug Administration (FDA). These organisations collect reports on the side effects of drugs from multiple sources, such as patients, pharmacists, physicians, and pharmaceutical manufacturers. Moreover, regulatory governmental agencies have set up reporting systems that allow the general public to report unintended side effects of using a drug. Recently, software-based solutions have been employed in order to optimise the process and storage of any generated report from the public.

Due to the cost and time required by the pre-clinical tri is, many drugs are release with undiscovered side effects. For this reason, after a drug is released its side effects are mainly discovered by chance due to adverse patient reactions. More recently, attempts have been made to design techniques and methods that allow such events to be discovered prematurely, avoiding damage to patients. This has been done by using available data, such as historical reports, to try to determine causalities, inferences and correlations.

Existing software systems that predict the occurrence of a side effect with the use of a certain drug(s) are mainly based on post-market data or generated after commercialisatiom In this regard, such data may include: patient's data, adverse events reports from the general public, or post-marketing statistics. The systems require the availability of such data in order to operate. Despite this, existing methods have the following characteristics/drawbacks, which have been classified by the inventors into four groups, as follows:

1. "Post-Marker" methods that require the release of a drug openly to the market in order to collect, after the release, medical feedback from stakeholders (for example, reporting agencies, patients). These methods mainly rely on statistical inference that is detected through adverse event incidents, i.e. after the side effect has been endured by patients. These methods can also contain a significant time lag between side effects being experienced and being reported to agencies. Moreover, to collect such feedback from a statistically significant sample requires a lot of time and effort, causing further delays and potentially endangering the general public.
2. "Patient data" based methods require the collection of personal and confidential data from patients. These methods are intrusive in nature and are high cost due to the different legal steps that are needed to acquire such data. These methods tend to be associated with very expensive clinical trials and patient monitoring, and are generally high-risk in case of undocumented uses of a drug.
3. "Small data" methods where side effects are predicted based on small dimension vectors of features extracted from a single drug. For example, these methods do not take into account characteristics of multiple drugs at the same time, and the side effects associated with those drugs.
4. "Complete data" methods in which a set of required characteristics (features) are needed for the method to operate. In these methods, each drug under question has to undergo thorough investigations in order to determine the intrinsic characteristics needed. In many scenarios, drug manufacturers and regulatory agencies may not have all these characteristics and thus predicting side effects would not be possible.

Embodiments of the present invention try to overcome the above mentioned drawbacks, through a method that i) is an early detection method which utilises data available prior to market release, and/or ii) exploits low-cost data usage by utilising open access data and not relying on or requiring patient data and/or experimental trials, and/or iii) is capable of operating with incomplete data while allowing for the incremental integration of knowledge acquired through the drug manufacturing process and/or other stakeholders.

According to an embodiment of one aspect of the invention, there is provided a similarity-computation apparatus configured to use open data to compute similarities between drugs, the apparatus comprising: a data integration module configured to obtain data related to a set of drugs from a plurality of open data sources and to integrate the data to generate RDF triples; an RDF module configured to store an RDF graph of the RDF triples; and a similarity calculation module configured to retrieve a list of all the drugs present in the RDF graph and calculate the similarity of each drug with every other drug in the RDF graph.

Since the method learns from known side effects identified for drugs in the past, the more drugs the system contains the better. However, the set of drugs may correspond to a specific medical treatment or sub-group, omitting other drugs.

RDF provides the connections between drugs for the method of invention embodiments to work. Data in other data formats such, as relational databases, CSV files, JSON files, etc., can be used with a corresponding mapping to RDF.

Invention embodiments use open data to provide drug similarity data from an integrated RDF graph, which can then be used in a similarity-computation apparatus (described later) to extrapolate side effects of a specified drug from other drugs.

RDF (Resource Description Framework) is a general method for conceptual description or modelling of information that is a standard for semantic networks. Standardising the modelling of information in a semantic network allows for interoperability between applications operating on a common semantic network. RDF maintains a vocabulary with unambiguous formal semantics, by providing the RDF Schema (RDFS) as a language for describing vocabularies in RDF.

The triples provide for encoding of graph data by characterising the graph data as a plurality of subject-predicate-object expressions. In that context, the subject and object are graph nodes of the graph data, and as such are entities, objects, instances, or concepts, and the predicate is a representation of a relationship between the subject and the object. The predicate asserts something about the subject by providing a specified type of link to the object. For example, the subject may denote a Web resource (for example, via a Unique Resource identifier, URI), the predicate denote a particular trait, characteristic, or aspect of the resource, and the object denote an instance of that trait, characteristic, or aspect (perhaps another URI). In other words, a collection of triple statements intrinsically represents directional graph data. The RDF standard provides formalised structure for such triples. An RDF graph can be queried using the SPARQL Protocol and RDF Query Language (SPARQL).

Preferably, the data integration module is configured to allow integration of new data during runtime (that is after an initial set-up), and the RDF module is configured to add the new data to the RDF graph. The new data may be from existing data sources or from new data sources. The data sources do not necessarily need to be expressed in RDF initially; they can be converted into RDF using a mapping language. The source can be a relational database, a CSV (comma-separated value) file, a JSON (JavaScript Object Notation) file, etc.

The data integration module may be configured to recognise alternative terms for the same drug and to class all the data associated with the alternative terms together as longing to the same drug. For example, the module may use ontology web language (OWL) to automatically process downloaded language, for example to define a "same as" relationship.

The data integration module may be configured to use alternative names, synonyms and string distance measures to recognise alternative terms for the same drug.

Furthermore, the data integration module may be configured to link together different instances of the same drug, for example by using a unique identifier. All these features taken together can allow successful integration of data from different sources.

For example, the data integration module may be configured to integrate data from one or more of drug property, side effects, drug classification and diseases databases. The list of databases can be expanded to include further databases.

Turning to the similarity calculation module, this uses RDF functionality to calculate similarity. For example, it may be configured to find a set of predicates and objects/subjects of RDF triples in which, for each drug, the drug is a subject or an object respectively and to generate a feature vector from the predicates and objects/subjects representing the features of the drug, wherein the similarity calculation module is further configured to calculate the similarity of each drug with every other drug in the RDF graph by comparison of the feature vectors of the two drugs. In this context, each of the n predicate and object/subject combinations can be viewed as a feature and the feature vector can be viewed as an n-dimensional vector.

Side effects can be included in the computation of similarities or not, they are not a requirement for the method to work. Any attribute of a drug can be used as a feature to compute the similarity including side effects (if any). If the method is applied over a new drug without any previous known side effects, the method will report new side effects just based on its chemical composition. If the method is applied to an existing drug with side effects, the method will report extra side effects. The method is designed to work with partial data.

The similarity calculation module may be configured to calculate the similarity between two drugs by eking into account the number of intersecting features of the feature vectors, in which the predicate and the subject or object (which makes up the triple together with the drug) is the same for both drugs. Hence, in the triples being compared, the drugs are different but the predicate and third element (subject or object) in the triple are the same.

The similarity calculation module may be configured to store the calculated similarities as drug-drug distances for the set of drugs in a similarity database to which the similarity-computation apparatus is connected.

According to an embodiment of a further aspect of the invention, there is provided a side effect determining apparatus which uses the calculated similarities to look for potential side effects. The side effect determining apparatus may thus be configured to extrapolate side effects of a specified drug in a set of drugs from open data related to the set of drugs. The apparatus can comprise: a connection to a similarity database, the similarity database being configured to store similarity data derived from a plurality of open data sources, the similarity data providing drug similarity between each drug and every other drug in a set of drugs; a user interface configured to allow a user to specify a drug from the set of drugs; a neighbours ranking module configured to use the drug similarities to obtain nearest neighbours of the specified drug in terms of the similarities; and a side effects propagation module configured to collect known side effects from the nearest neighbours and to combine and rank the side effects according to their co-occurrence among the neighbours.

Hence the side effect determining apparatus does not rely on any side effects which may be indicated for the specified drug, but looks to the closest drugs to the specified drug, based on the similarity data, and propagates the side effects of these most similar drugs, using a ranking method.

The similarity data may be provided as drug-drug distances in a vector space model in an n-dimensional space, and the neighbours ranking module may be configured to select k nearest neighbours on the basis of distances within the n-dimensional space.

The side effects propagation module may be configured to compute the frequency of drug features occurring with each side effect found among the known side effects to build a correlation between each side effect and each drug feature.

For example, the drug features may include any of drug properties, drug classification and diseases, which are already included in the similarity data. The features used here can be the same as those used to compute the similarity data, or a sub-group of the features. The processing of the features is different here in the function applied. Clearly side effects are now the pivots.

The side effect determining apparatus may comprise a notification module configured to issue a warning, alarm or notification with a list of side effects and/or if certain (for example more serious or specified) side effects are extrapolated.

According to an embodiment of a still further aspect of the invention, there is provided a system for calculating similarities between drugs and using the similarities to extrapolate side effects of a specified drug. The system is effectively a combination of the similarity-computation apparatus and the side effect determining apparatus. It may thus comprise: a similarity-computation apparatus configured to use open data to compute similarities between drugs, the similarity-computation apparatus comprising: a data integration module configured to obtain data related to a set of drugs from a plurality of open data sources and to integrate the data to generate RDF triples; an RDF module configured to store an RDF graph of the RDF triples; and a similarity calculation module configured to retrieve a list of all the drugs present in the RDF graph and to calculate the similarity of each drug with every other drug in the RDF graph, for storage in a similarity database; and a side effect determining apparatus configured to extrapolate side effects of a specified drug from open data related to the set of drugs, the side effect determining apparatus comprising: a connection to the similarity database; a user interface configured to allow a user to specify a drug from the set of drugs; a neighbours ranking module configured to use the drug similarities to obtain nearest neighbours of the specified drug in terms of the similarities; and a side effects propagation module configured to collect known side effects from the nearest neighbours and to combine and rank the side effects according to their co-occurrence among the neighbours.

Any sub-features of the similarity-computation apparatus and the side effect determining apparatus may be incorporated into the system as initially described above.

According to an embodiment of a first method aspect of the invention, there is provided a method of using open data to compute similarities between drugs, the method comprising: obtaining data related to a set of drugs from a plurality of open data sources; integrating the data to generate RDF triples; storing an RDF graph of the RDF triples; retrieving a list of all the drugs present in the RDF graph; and calculating the similarity of each drug with every other drug in the RDF graph.

According to an embodiment of a second method aspect of the invention, there is provided a method of extrapolating side effects of a specified drug from open data related to a set of drugs, the method comprising: user input specifying a drug from the set of drugs; obtaining nearest neighbours of the specified drug in terms of the similarities using a similarity database configured to store similarity data derived from a plurality of open data sources, the similarity data providing drug similarity between each drug and every other drug in the set of drugs; collecting known side effects from the nearest neighbours; and combining and ranking the side effects according to their co-occurrence among the neighbours.

The two method aspects may be carried out by the same person or commercial entity, or by different people/commercial entities.

The invention can be implemented in digital electronic circuitry, or in computer hardware, firmware, software, or in combinations of them. The invention can be implemented as a computer program or computer program product, i.e., a computer program tangibly embodied in an information canner, e.g., in a machine-readable storage device or in a propagated signal, for execution by, or to control the operation of, one or more hardware modules. A computer program can be in the form of stand-alone program, a computer program portion or more than one computer program and can be written in any form of programming language, including compiled or interpreted languages, and it can be deployed in any form, including as a stand-alone program or as a module, component, subroutine, or other unit suitable for use in a communication system environment. A computer program can be deployed to be executed on one module or on multiple modules at one site or distributed across multiple sites and interconnected by a communication network.

Method steps of the invention can be performed by one or more programmable processors executing a computer program to perform functions of the invention by operating on input data and generating output. Apparatus of the invention can be implemented as programmed hardware or as special purpose logic circuitry, including e.g., an FPGA (field programmable gate, array) or ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for executing instructions coupled to one or more memory devices for storing instructions and data.

The invention is described in terms of particular embodiments. Other embodiments are within the scope of the following claims. For example, the steps of the invention, can be performed in a different order and still achieve desirable results.

The apparatus according to preferred embodiments is described as configured or arranged to carry out certain functions. This configuration or arrangement could be by use of hardware or middleware or any other suitable system. In preferred embodiments, the configuration or arrangement is by software.

Elements of the invention have been described using terms such as "module". The skilled reader will appreciate that these terms and their equivalents may refer to parts of the system that are spatially separate but combine to serve the function defined. Equally, the same physical parts of the system may provide two or more of the functions defined.

Features and sub-features of the system and apparatus aspects may be applied to the method aspects and vice versa

BRIEF DESCRIPTION OF THE DRAWINGS

Reference made, by way of example only, to the accompanying drawings in which:

FIG. 1 shows block diagram of a similarity-computation apparatus according to a general embodiment of the present invention. The similarity-computation apparatus may be embodied as a server or a PC or another computing apparatus with connection via the internet. It comprises a data integration module 105, an RDF module 106 and a similarity calculation module 107. The similarity-computation apparatus also has access to one or more open data sources 100 (databases or more simple data stores). The similarity-computation apparatus may be directly or indirectly connected to the open data source(s) 100, through a suitable network connection (for example over the internet). Alternatively or additionally, the similarity-computation apparatus may comprise one or more local data sources. The open data source 100 may comprise one or more of: a drug profile database 101; and/or a side effect database 102; and/or a drug classification database 103; and/or a disease database.

Figure 1:
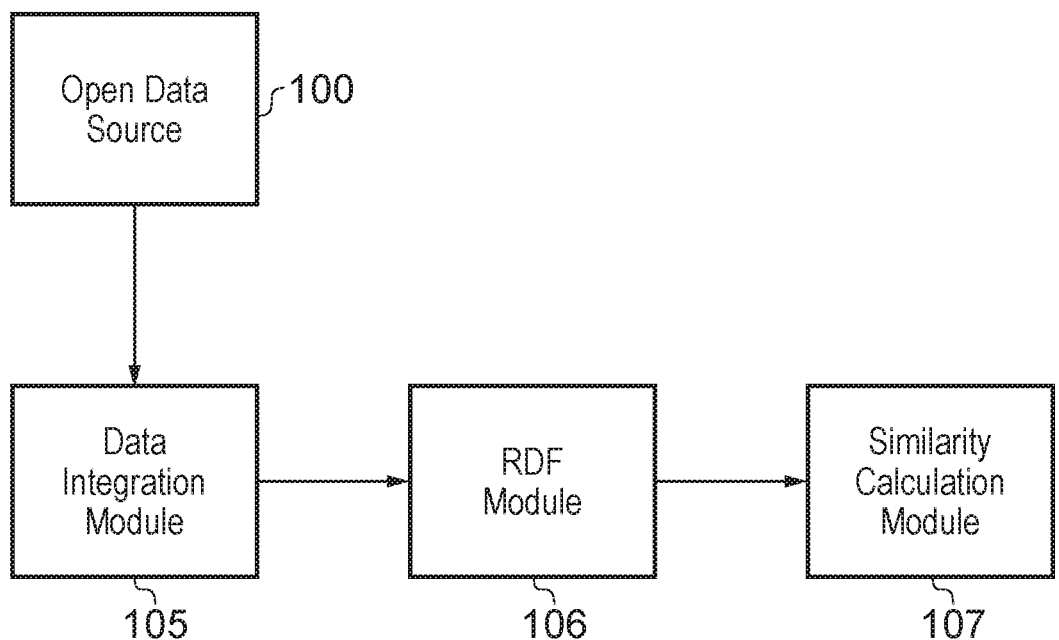
FIG. 1 is an apparatus block diagram representing a similarity-computation apparatus according to a general embodiment of the invention.

The similarity-computation apparatus uses open data to compute similarities between medicaments. Firstly, the data integration module 105 obtains data, which relates to a set of two or more medicaments (for example, drugs), from the open data source 100. The data relating to the set of drugs is then integrated by the data integration module 105 to generate RDF triples for each of the drugs in the set of drugs. The data integration module 105 may also, when integrating the data, filter and/or join the data. The RDF triples relating the data for the set of drugs are then transferred to the RDF module 106.

The RDF module 106 stores an RDF graph of the RDF triples generated by the data integration module 105. The similarity calculation module 107 then uses the RDF graph stored on the RDF module 106 to retrieve a list of all the drugs that are contained in the RDF graph. The similarity calculation module 107 then calculates the similarity of the drugs contained in the set of drugs with the other drugs in the drug set. For example, for a set of drugs containing drugs A, B and C, the similarity calculation module 107 may calculate the similarity between drug A and drug B, the similarity between drug A and drug C, and the similarity between drug B and drug C. These calculated similarities can be stored in a similarity database 109 (not shown).

Figure 2:
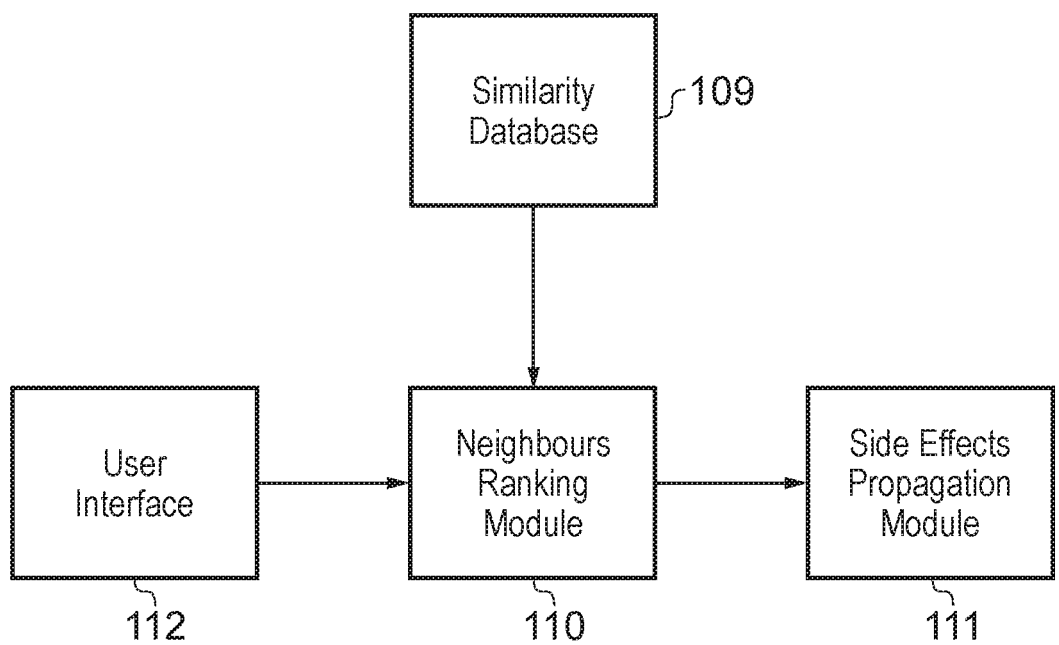
FIG. 2 is an apparatus block diagram representing a side effect determining apparatus according to a general embodiment of the invention.

FIG. 2 shows a block diagram of a side effect determining apparatus according to a general embodiment of the present invention. The side effect determining apparatus may be a server or a PC or another computing apparatus with connections via the internet. It comprises a user interface 112, a neighbours ranking module 110 and a side effects propagation module 111. The side effect determining apparatus also has access to one or more similarity databases 109. The side effect determining apparatus may be directly or indirectly connected to the similarity database(s) 109, through a suitable network connection. Alternatively or additionally, the side effect determining apparatus may further comprise one or more local similarity databases 109. The similarity database 109 is capable of storing similarity data relating to the similarity between each drug of a set of drugs and every other drug in the set.

The side effect determining apparatus is capable of determining side effects (or potential/probable side effects) associated with a specified medicament (or drug). The user interface 112 allows a user to specify a particular drug from the set of two or more drugs. The specified drug is then transferred to the neighbours ranking module 110, which uses the similarity data stored in the similarity database 109 to obtain the drugs from the drug set that are the nearest neighbours of the specified drug in terms of similarities.

The side effects propagation module 111 is then able to collect a list of known side effects from the selected nearest neighbours to the specified drug. The side effects in the list are combined and ranked by the side effects propagation module 111, according to their co-occurrence among the neighbour drugs. That is, the side effects that are more likely to be associated with the specified drug are ranked higher than those that are not.

Figure 3:
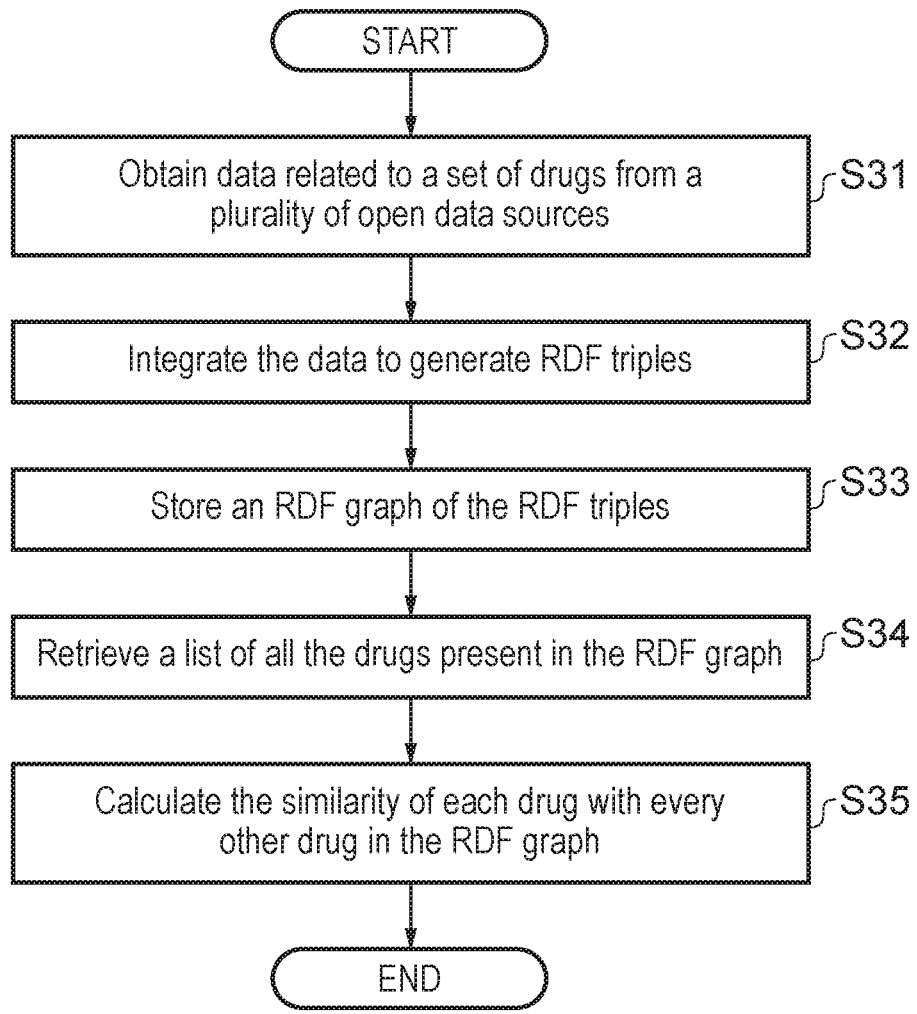
FIG. 3 is a flow chart of the method in the similarity-computation apparatus according to a general embodiment of the invention.

FIG. 3 is flow chart representing the method in the similarity-computation apparatus according to a general embodiment of the present invention. Firstly, in step S31 data relating to a set of two or more drugs is acquired from one or more open data sources. The acquired data is then integrated and RDF triples for the set of drugs are generated in step S32. An RDF graph of the RDF triples is stored in step S33, in order to be accessed in step S34 when calculating the similarity of each drug in the set of drugs with every other drug in the drug set in step S35.

Figure 4:
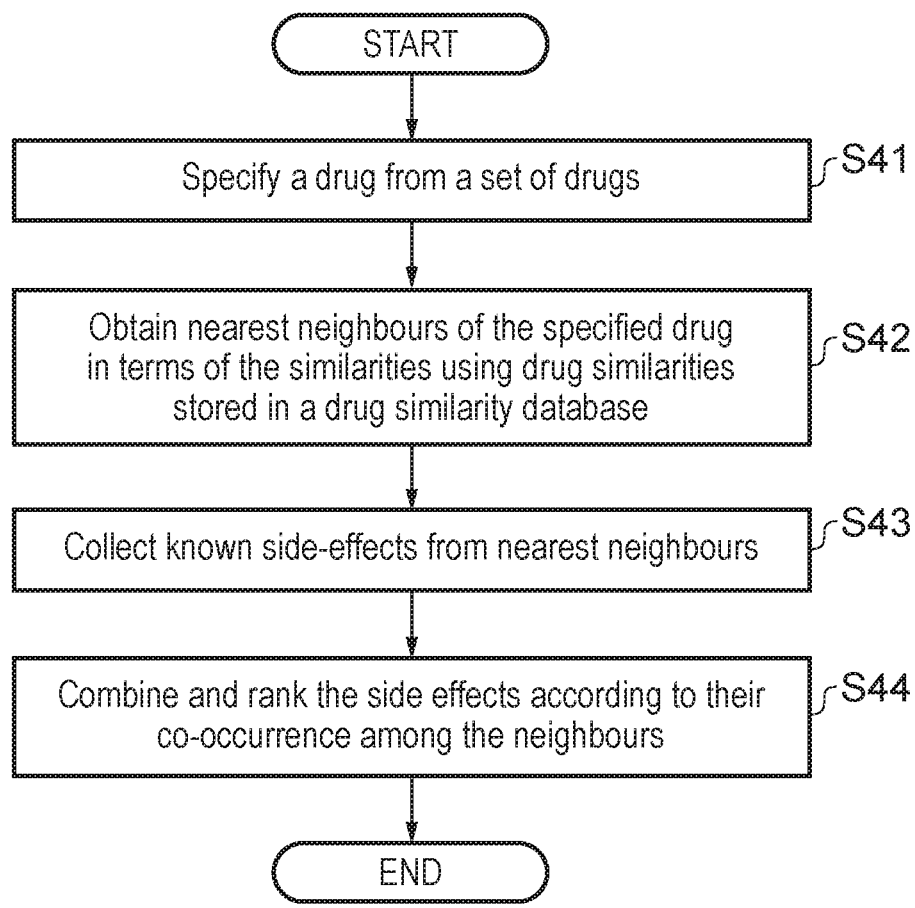
FIG. 4 is a flow chart of the method in the side effect determining apparatus according to a general embodiment of the invention.

FIG. 4 is a flow chart representing the method in the side-effect determining apparatus according to a general embodiment of the present invention. Firstly, in step S41 a drug is specified, preferably by a user, from a set of two or more drugs. Drug similarities stored in a drug similarity database are then used in step S42 to determine the drugs from the drug set that are the nearest neighbours of the specified drug in terms of similarities. Next, a list of known side effects of the nearest neighbour drugs to the specified drug are collected in step S43. The collected side effects are then combined and ranked in step S44 according to their co-occurrence among the neighbour drugs.

The method of invention embodiments may be seen as two-fold: 1) a drug-centric view in which all data available for drugs is used to compute similarity between drugs and 2) a side effect centric view where co-occurring side effects are used to determine occurrence probabilities of a side effect in other drugs. The former approach may be used to identify true positives side effects for a given drug, while the latter approach may be used for detecting false negatives in the data, i.e., side effects that have no possibility of being associated with certain drugs. This novel configuration allows the method herein presented with the filtering of noise in the output results, resulting in better prediction results.

Particular embodiments of the present invention described herein make use of knowledge, in the form of Linked Data (machine readable), for discovering unknown potential side effects of a drug. Notifications, alerts or warning signals may then be emitted or communicated as a result. Major initiatives and governments are publishing such data as open access data on the Web. Linked Open Data (LOD) is a paradigm in which linked data from a variety of sources is made available to applications, thus, for the purposes of this document, "Linked Data" and "Linked Open Data" or "LOD" may be used more or less interchangeably.

This is in contrast to current approaches known in the art, which make use of data sources which are slower to gather, such as, for example, agencies reports, and/or intrusive personal patients' data, and/or risky patients' reaction reports. Furthermore, embodiments of the present invention may also allow the feeding of other or newer data sources, such as side effect reports and biomedical literature. This may require the application of proper join and filtering processes.

The signalling process can be compared with a recommender system, retrieving weighted warning (recommendations) for potential side effects (items) caused by a drug (users). The embodiments of the present invention take advantage of structured data in order to compute similarity between drugs that are used and to suggest potential side effects for a drug.

Figure 5:
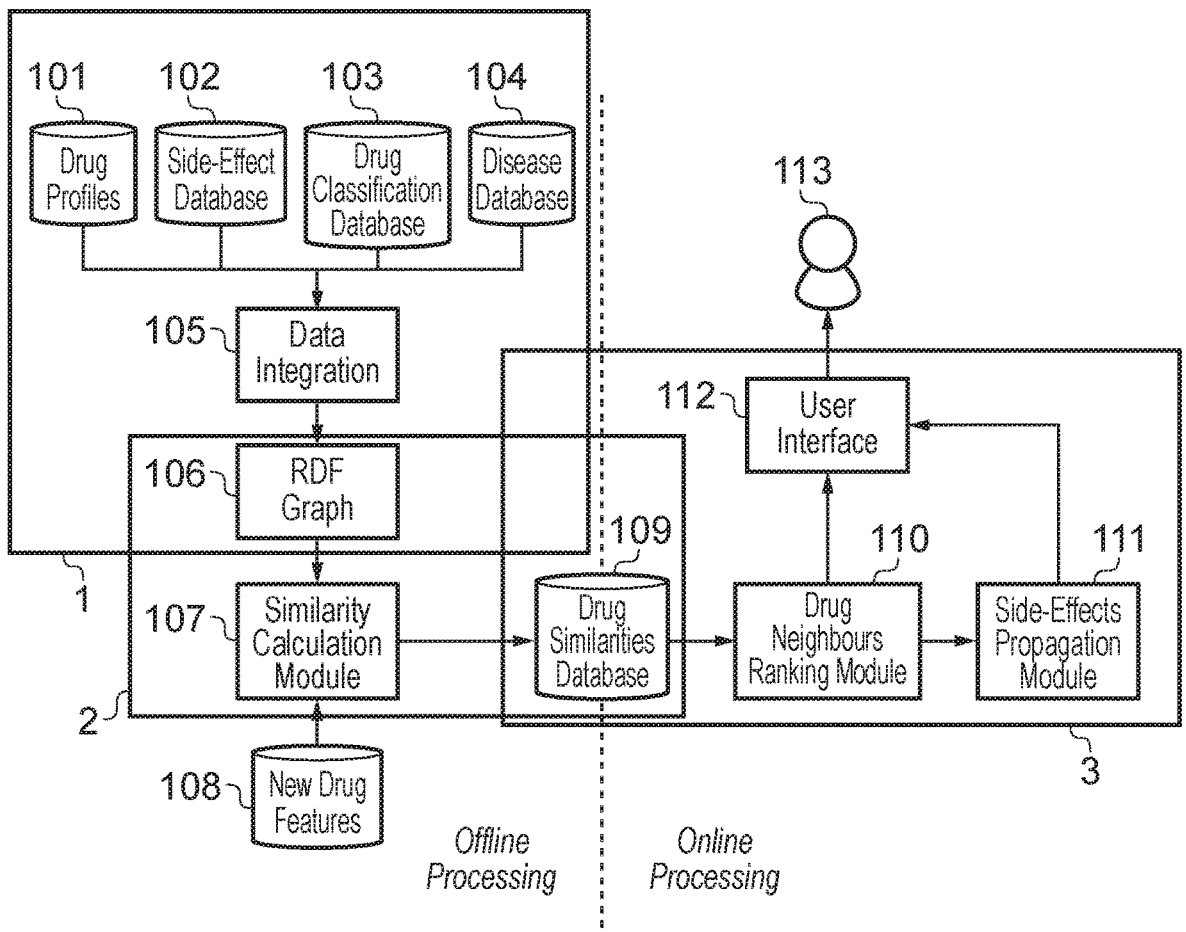
FIG. 5 is a blocklflow diagram representing an example system/architecture according to an embodiment of an aspect of the invention.

FIG. 5 shows a block diagram with information flows representing an example system/architecture for using Linked Data to discover drug side effects according to an embodiment of an aspect of the invention. In general, the method has two stages: one stage (shown on the left side of FIG. 5) that is, due to the processing time required, preferably executed offline in a suitable server machine to satisfy the query requirements; and a second stage (shown on the right side of FIG. 5) that is preferably executed completely or partially online, allowing users to access and visualise detected signals or associations between drugs and side effects. In terms of flow, the process can be separated into the three main blocks shown in FIG. 5 and discussed below. These blocks are: (1) knowledge base construction, (2) similarity computation, and (3) side effect signalling.

1) Knowledge Base Construction

The present invention proposes a novel method for signal detection of drug side effects using Open Data. Known diverse initiatives focus on the transformation and publication of Life Sciences data using an open, exchangeable and flexible data format such as Resource Description Framework (RDF), Linked Data builds upon RDF (used as data model), HTTP (used to transfer data via the Internet), and uniform resource identifier (URI) (used to identify resources) in order to publish data in a way that can be read automatically by computers.

In a preferred embodiment of the invention, RDF is used as the data format to represent a graph which represents the underlying drug-related background knowledge sources. Despite the fact that some data sources are not originally published as RDF or are incomplete transformations, in this work a non-trivial data extraction, transformation and integration process was carried out. For instance, the same drug can be contained in different data sources with a different name or spelling, which makes it impossible to perform a direct string match. This problem is addressed by matching drugs and side effects' names, using a more complex matching which is based on alternative names and synonyms. To mention, two examples:

1) The inventors generated a more complete RDF dump from the Side Effect Resources Sider (www.sideeffects.embl.de/) by extending it with Automatic Taxonomy Construction, ATC taxonomy to generate a hierarchical outline, Medical Dictionary for Regulatory Activities (MedDRA) preferred terms, and frequency of the side effects extracted from their public website.

2) The inventors integrated drugs' names from the resource DrugBank (www.drugbank.ca/) with Sider, and side effects' names from Sider with Diseasome (www.diseasome.eu/), using alternative names (owl:sameAs relationship), synonyms, and string distance measures.

As shown in FIG. 5, various data sources may be considered, such as, for example, drug profiles (101), side effect database (102), drug classification database (103), and/or disease database (104). The data sources are integrated by the Data Integration module (105), to later make them available through an RDF Graph (106) to be queried. The data sources used are not limited to the above listed examples and different public sources, such as post-market reports, can also be used in the present method to build an RDF Graph knowledge base. Due to the RDF flexibility, other unstructured sources containing drugs' properties (for example, chemical, biological, phenotypic information), side effects, drug classification, and diseases, can also be utilised. The initially mentioned sources are openly available to users, thus minimising the costs of data gathering and the overall method.

Figure 6:
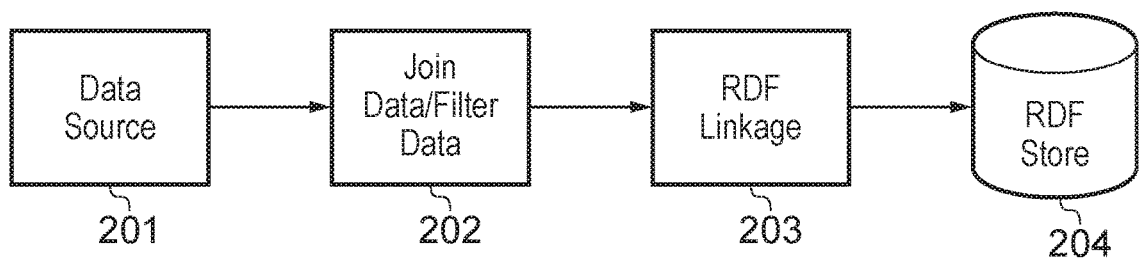
FIG. 6 is a block diagram showing the interaction between a Data integration module and RDF Graph module according to an embodiment of an aspect of the invention.

FIG. 6 shows an extended view of the interaction between the Data, integration module (105) and the RDF Graph module (106). The Data integration module (105) is responsible for processing a data source (201) and for performing data integration with filtering in order to generate RDF triples. The RDF triples are then stored and indexed in an RDF store (204) for future querying. Data sources usually require a linkage process (203) to make the same entities accessible using a unique identifier. That is, if a drug contains alias names, the system needs to ensure that whatever alias is used, the drug identifier retrieved is the same. This avoids reference problems and keeps an acceptable integrity level in the data.

2) Similarity Computation

The Similarity Calculation module (107) is the module responsible for computing drugs' similarity. First, the Similarity Calculation module (107) retrieves a list of all drugs present in the RDF Graph (106). An RDF Graph is a directed graph in which each edge is an RDF triple with a (subject, predicate, object) structure and where the edge starts in the subject node and ends in the object node. Then, for each drug X in the list, the Similarity Calculation module (107) performs a query against the RDF Graph module (106) asking for the set of predicates (relations) where X is in a subject or an object position. Formally, using a query by patterns we could represent these queries as (X, ?, ?) and (?, ?, X) for subject and object, respectively. From those predicates a set of features for drug X is generated, which is referred to as a feature vector.

The RDF graph is a directed graph, i.e., the edges have a direction and there exist incoming and outgoing edges. Thus, the query (X, ?, ?) is used for outgoing edges, and the query (?, ?, X) is used for incoming edges, respectively.

Each drug is then associated to a feature vector extracted from the underlying RDF graph in 106. These features interact with the features of other drugs to compute a similarity between any given pair of drugs, in a preferred embodiment, the feature vectors and similarities for a pair of drugs may be generated as described below and with reference to FIG. 7.

Figure 7:
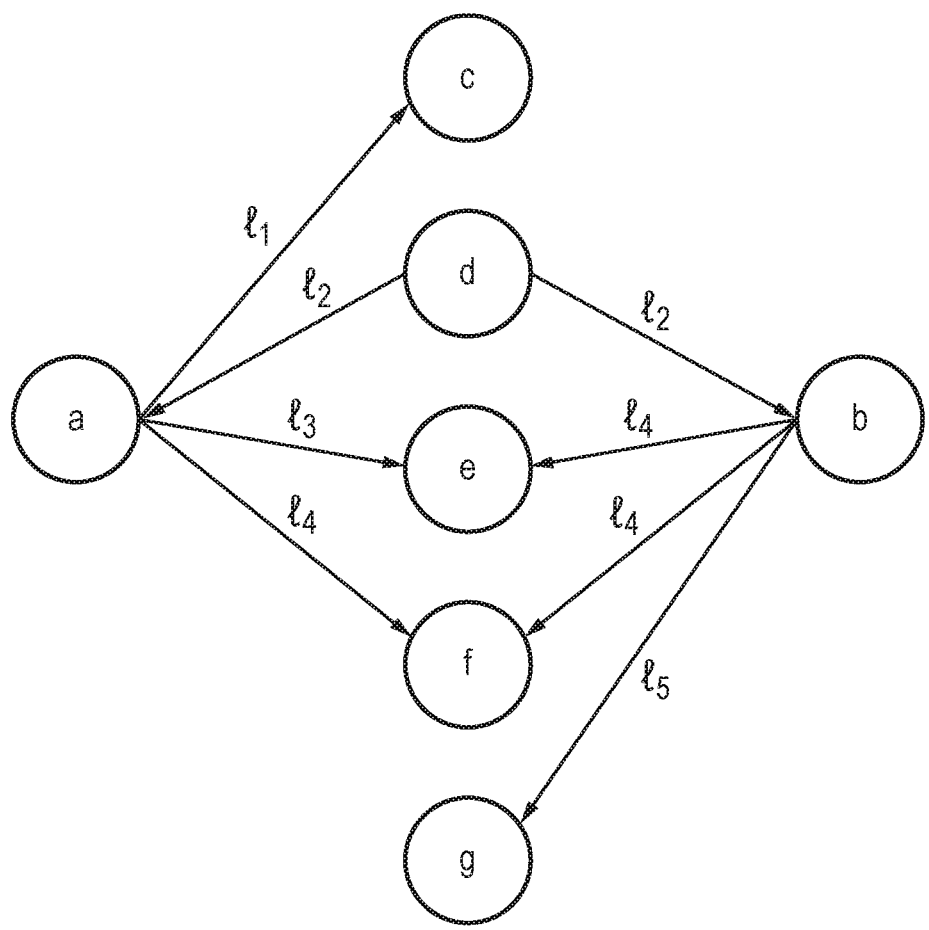
FIG. 7 is a schematic diagram of an example RDF graph according to an embodiment of an aspect of the invention.

FIG. 7 shows an RDF Graph for two drugs, known as resources in the RDF Graph domain. The similarity of the two drugs of the RDF graph shown in FIG. 7, a and b, is to be calculated, in this example, a similarity metric based on the work described in R.

Meymandpour and J. G, Davis, "Recommendations Using Linked Data," in PIKM, Maui, Hi., 2012, is used, however, any other suitable metric may be adapted in order to compute similarity between resources in an RDF graph.

Let A be the set of features for the resource a, where A contains two sets: one set for outgoing and another for incoming edge relations, i.e. A={{outgoing},{incoming}}. Resource a in FIG. 7 has outgoing relations to resources c, e, and f with predicates $l_1$, $l_3$ and $l_4$, respectively. Also, it has incoming relations from the resource d with predicate $l_2$. Then, A is defined as shown in Equation (1) below.

$$A = \text{Features}_{LD}(a) = \{\{(l_1,c),(l_3,e),(l_4,f)\},\{(l_2,d)\}\} \quad (1)$$

Similarly, B is defined as the set of features for the resource b, as shown in Equation (2).

$$B = \text{Features}_{LD}(b) = \{\{(l_4,e),(l_4,f),(l_5,g)\},\{(l_2,d)\}\} \quad (2)$$

Intuitively, the more elements a and b have in common, the more similar they are. This is consistent with the principles of feature-based metrics, where a higher level of shared features implies a higher similarity value. Thus, to compute the similarity between a pair of resources in the RDF graph we use the intersection between feature sets. For example, the intersection between A and B is given by Equation (3).

$$A \cap B = \{\{(l_4,f)\},\{(l_2,d)\}\} = C \quad (3)$$

In the associated prior art, "Recommendations Using Linked Data," similarity is defined using Information Theory methods to identify the significance of features based on their probabilities.

$$\text{Similarity}(A,B) = IC_{LD}(C) \quad (4)$$

The Information Content (IC) of a set of features in Linked Dat (LD) is then defined as the sum of the IC of each component in the vector.

$$IC_{LD}(A) = \sum_{\forall a_i \in A} IC(a_i) \quad (5)$$

For a component in the vector, its IC is computed as normalized frequency score.

$$IC_{\forall a_i \in A}(a_i) = -\log\left(\frac{\varphi(a_i)}{n}\right) \quad (6)$$

Where $\varphi(a_i)$ is the frequency of feature a in the RDF graph and n is the maximum number of occurrences of a feature.

Figure 8:
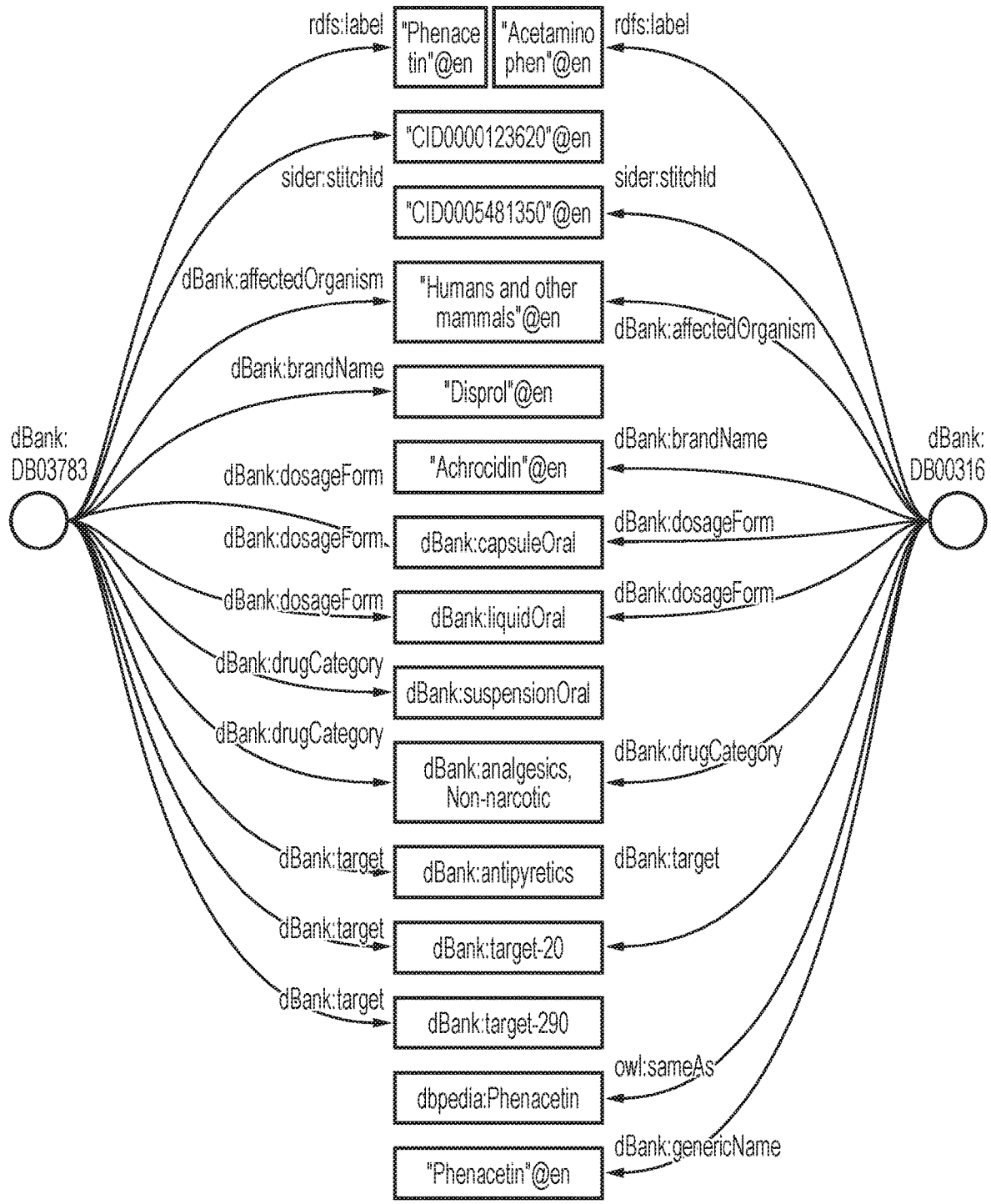
FIG. 8 is an example subset of elations for two drugs according to an embodiment of an aspect of the invention.

Shown in FIG. 8 and discussed below is a detailed example for two drugs: Phenacetin (identified by dBank: DB03783) and Acetaminophen (identified by dBank: DB00316), with a subset of their relations including: label, brand name, dosage form, and target proteins. As can be seen in FIG. 8, drugs dBarik:DB03783 (Phenacetin) and dBank: DB00316 (Acetaminophen) share some relations with the following literals and resources: "Humans and other mammals"@eri, dBank:capsuleOral, dBank:liquidOral, dBank:analgesics,Non-narcotic, dBank:target-20.

The list of five relations shared by the two drugs is:
dBank:affectedOrganism
dBank:dossageForm (twice)
dBank:drugCategory
dBank:target Based on these relations the corresponding feature vectors can be computed, and a similarity score between dBank: DB03783 (Phenacetin) and dBank:DB00316 (Acetaminophen) determined.

$$A = \text{Features}_{LD}(dBank: DB03783) \quad (7)$$

$$= \left\{\left\{\begin{array}{l}(rdfs:\ \text{label, "Phenacetin"}@en),\\(sider:\ stitchid,\ "CID0000123620"@en),\\\left(\begin{array}{l}dBank:\ affectedOrganism,\\ \text{"Humans and other mammals"}@en\end{array}\right),\\(dBank:\ brandName,\ "Disprol"@en),\\(dBank:\ dosageForm,\ dBank:\ capsuleOral),\\(dBank:\ dosageForm,\ dBank:\ liquidOral),\\(dBank:\ dosageForm,\ dBank:\ suspensionOral),\\\left(\begin{array}{l}dBank:\ drugCategory,\ dBank:\ \text{analgesics,}\\ \text{Non-narcotic}\end{array}\right),\\(dBank:\ drugCategory,\ dBank:\ \text{antipyretics}),\\(dBank:\ target,\ dBank:\ target-20),\\(dBank:\ target,\ dBank:\ target-290)\end{array}\right\},\phi\right\}$$

$$B = \text{Features}_{LD}(dBank: DB00316) \quad (8)$$

$$= \left\{\left\{\begin{array}{l}rdfs:\ \text{label, "Acetominophen"}@en),\\(sider:\ stitchid,\ "CID0005481350"@en),\\\left(\begin{array}{l}dBank:\ affectedOrganism,\\ \text{"Humans and other mammals"}@en\end{array}\right),\\(dBank:\ brandName,\ "Achodin"@en),\\(dBank:\ dosageForm,\ dBank:\ capsuleOral),\\(dBank:\ dosageForm,\ dBank:\ liquidOral),\\\left(\begin{array}{l}dBank:\ drugCategory,\ dBank:\ \text{analgesics,}\\ \text{Non-narcotic}\end{array}\right),\\(dBank:\ target,\ dBank:\ target-20),\\(owl:\ sameAs,\ dbpedia:\ \text{Phenacetin}),\\(dBank:\ genericName,\ \text{"Phenacetin"}@en)\end{array}\right\},\phi\right\}$$

Thus, to get the similarity score between both drugs, the intersection between A and B needs to be computed, as shown in Equation 9.

$$A \cap B = \left\{\left\{\begin{array}{l}\left(\begin{array}{l}dBank:\ affectedOrganism,\\ \text{"Humans and other mammals"}@en\end{array}\right),\\(dBank:\ dosageForm,\ dBank:\ capsuleOral),\\(dBank:\ dosageForm,\ dBank:\ liquidOral),\\\left(\begin{array}{l}dBank:\ drugCategory,\ dBank:\ \text{analgesics,}\\ \text{Non-narcotic}\end{array}\right),\\(dBank:\ target,\ dBank:\ target-20)\end{array}\right\},\phi\right\} \quad (9)$$

$$= C$$

The intersection contains the set of shared features. Note that neither A or B contains incoming edges, so the right side set of features is empty. For each feature its information content is then computed to get a final similarity score.

Figure 9:
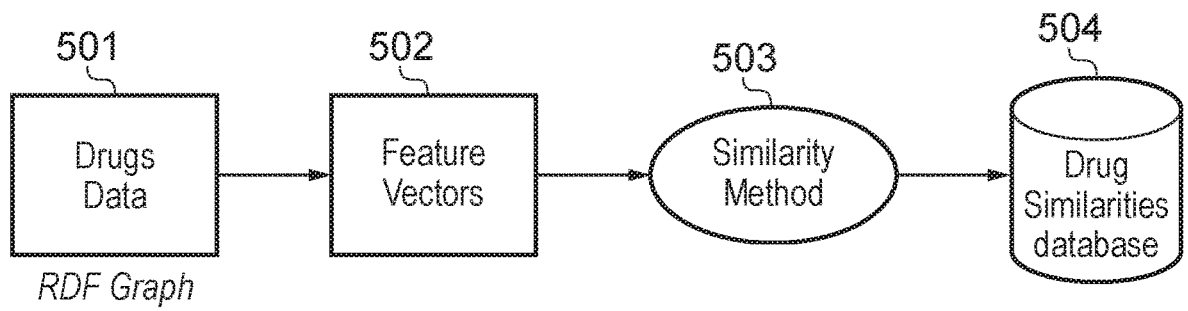
FIG. 9 is a block diagram of a Similarity Calculation module according to an embodiment of an aspect of the invention.

In summary, FIG. 9 shows fire grained block chart for the similarity calculation module. The Similarity Method (503) gets a set of Feature Vectors (502) as input, which were previously generated from the underlying RDF Graph with Drugs' Information (501). Drug similarities are stored in the Drug Similarities Database (504) to be consumed during the online processing under a user's request.

3) Side Effect Signaling

Note that during the similarity calculation process (107 in FIG. 5) a series of drug-to-drug distances are computed and stored in the drug similarities database (109 in FIG. 5 and 504 in FIG. 9), which is later used during the online part of the system.

Figure 10:
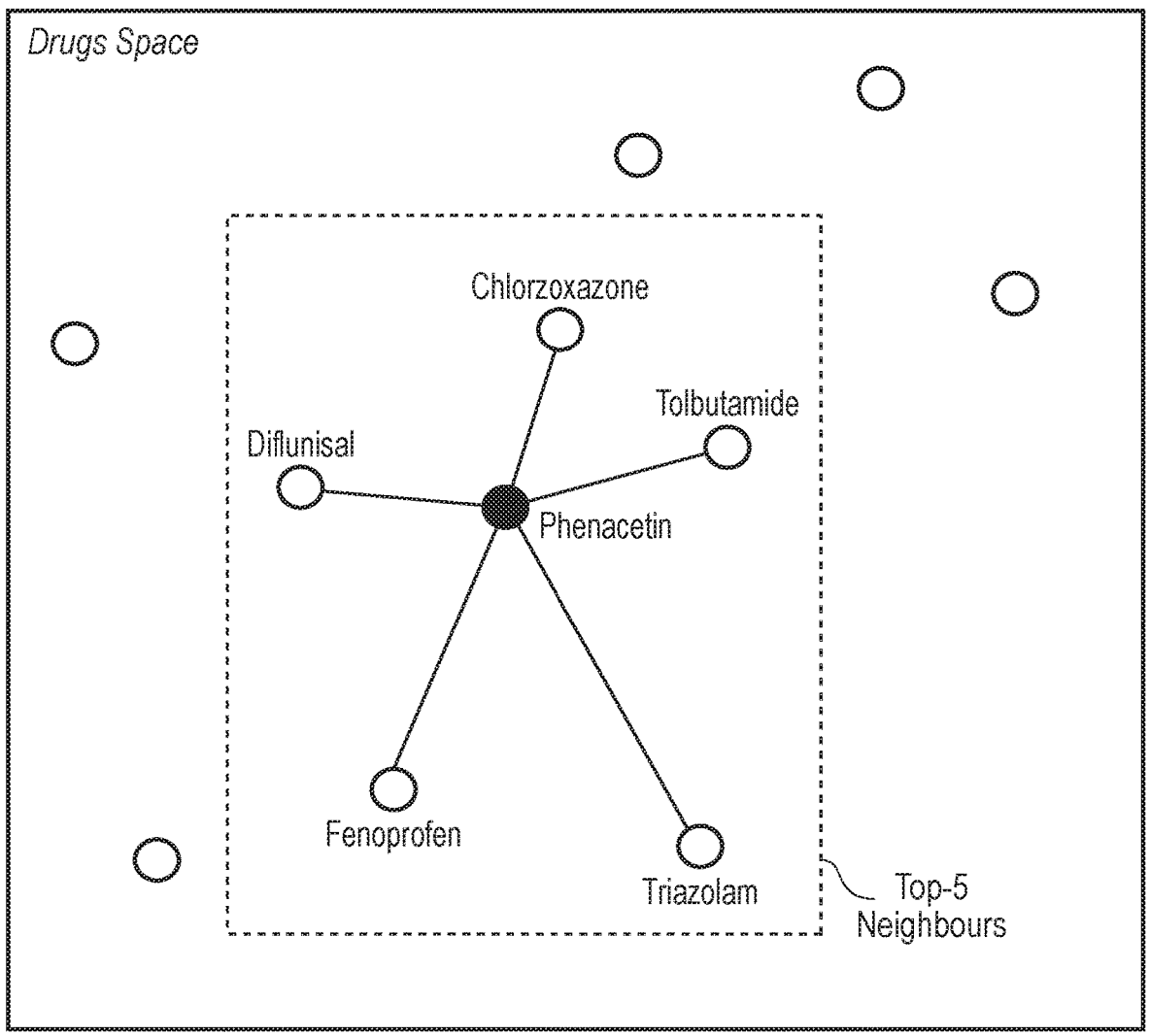
FIG. 10 is an example of a Drug Neighbours Ranking module according to an embodiment of an aspect of the invention.

Conceptually, the drug similarities database represents a vector space model where each drug is represented as a dot in a n-dimensional space (where n is the cardinality of the feature vectors), and certain properties are satisfied. FIG. 10 shows a small sample of this drugs space where the black dot denotes a selected drug, and the five connected non-filled dots are the top-5 more similar drugs, also called closest neighbours. This five plus one set of drugs conforms a neighbourhood where drugs are highly associated on the basis of their properties (for example, chemical, biological, or phenotypic information).

In order to determine a neighbourhood, the well known k-Nearest Neighbours (or k-NN) algorithm is used over a drug in order to get the k nearest neighbours. Here the value of k+1 represents the size of the neighbourhood.

Figure 11:
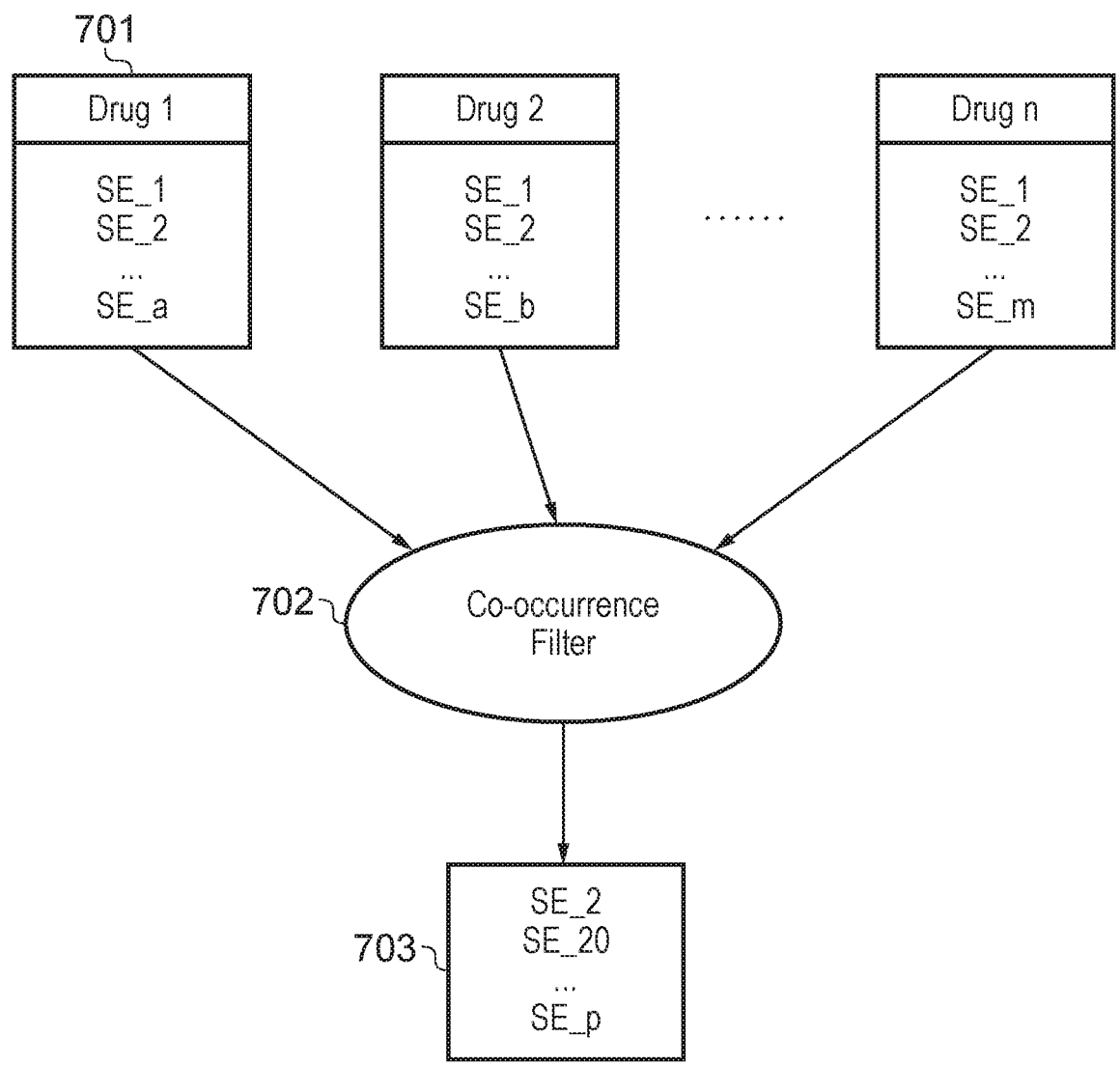
FIG. 11 is an example of a Side Effects Propagation module according to an embodiment of an aspect of the invention.

FIG. 11 depicts the Side Effects Propagation module (111) based on, a side, effect, based approach. For a given drug, the system collects the already known side effects among all its k neighbours (represented by 701). Side effects are combined and ranked according to their co-occurrence among the neighbour drugs to determine the signal's weight. Side effects may also be ranked using different ranking methods, not limited to the one described here.

The co-occurrence filter (702) computes the frequency of drug features occurring with each side effect. These features are used to build a normalised histogram of drug features for a given side effect. For example, the side effect abdominal pain occurs 271 times with known drugs, and only 5% of drugs that cause abdominal pain cure ventricular fibrillation; or 98% of drugs that cause abdominal pain contain chemical substructure 12. All these correlations can be expressed in a correlation matrix between all side effects and drug features. This correlation matrix is then used as a drug profile to rank side effects proposed by the neighbour drugs. The method herein described is therefore able to determine when a side effect is very unlikely to occur with the use of a given drug. For instance, using the profile matrix we could say that a drug manufactured to cure ventricular fibrillation that does not contain chemical substructure 12, and that targets the Q9NY47 protein is unlikely to cause abdominal pain.

Thus, side effects are selected by the co-occurrence filter (702) as potentially significant for a given drug, and a signal is emitted for each one of the potential side effects (703) to perform further analysis.

As an example, considering the extracted neighbourhood as discussed above and determining the side effects present in the top-5 neighbour drugs, the method can analyse the co-occurrences among the 5 drugs, to determine weights for the signals. A list of side effects is shown in Table 1 below.

TABLE 1

| | | |
|---|---|---|
| Acute anaphylaxis | Diarrhoea | Pruritus |
| Allergic cutaneous angillis | Dizziness | Rash |
| Chest pain | Dyspepsia | Renal failure |
| Disorientation | Dysuria | Somnolence |
| Dyspnoea | Fatigue | Stomatitis |
| Cramp muscle | Body temperature increased | Swealing |
| Nephrotic syndrome | Fasciitis | Thrombocytopenia |
| Palpitations | Flatulence | Tinnitus |
| Syncope | Flushing | Urticaria |
| Necrotising fasciitis | Gastritis | Vertigo |
| Hearing impaired | Gastrointestinal haemorrhage | Vomiting |
| Agranulocytosis | Hallucination | Hepatic function abnormal |
| Anaphylactic shock | Headache | Gastrointestinal perforation |
| Anaemia | Haematuria | Renal impairment |
| Haemolytic anaemia | Haemorrhage | Vision blurred |
| Angioedema | Hepatitis | Photosensitivity |
| Anorexia | Hypersensitivity | Hypersensitive syndrome |
| Asthenia | Jaundice | Visual disturbance |
| Bronchospasm | Nausea | Gastrointestinal pain |
| Cholestasis | Nephritis | Insomnia |
| Confusional state | Nephritis interstital | |
| Constipation | Nervousness | |
| Dermatitis | Oedema | |
| Dermattis exfoliative | Proteinuria | |

The highest ranked side effects, the ones with the greater, probabilities of occurring with the use of Phenacetin, are highlighted.

TABLE 2

| (a) | (b) |
|---|---|
| 1) Disorientation | 9) Dizziness |
| 2) Anaphylactic shock | 1) Disorientation |
| 3) Angioedema | 2) Anaphylactic shock |
| 4) Anorexia | 5) Confusional state |
| 5) Confusional state | 6) Constipation |
| 6) Constipation | 3) Angioedema |
| 7) Dermatitis | 4) Anorexia |
| 8) Diarrhoea | 7) Dermatitis |
| 9) Dizziness | 8) Diarrhoea |
| 10) Fatigue | 10) Fatigue |
| 11) Gastrointestinal haemorrhage | 20) Somnolence |
| 12) Haemorrhage | 11) Gastrointestinal haemorrhage |
| 13) Hypersensitivity | 12) Haemorrhage |
| 14) Jaundice | 13) Hypersensitivity |
| 15) Nausea | 14) Jaundice |

TABLE 2-continued

| (a) | (b) |
|---|---|
| 16) Nervousness | 15) Nausea |
| 17) Oedema | ~~16) Nervousness~~ |
| 18) Pruritus | 17) Oedema |
| 19) Rash | 18) Pruritus |
| 20) Somnolence | ~~19) Rash~~ |
| 21) Tinnitus | 21) Tinnitus |
| 22) Vomiting | 22) Vomiting |

Once the side effects are ranked, the co-occurrence filter helps to re-rank the side effects to give more importance to some side effects compared to others. Also the same filter helps to discard certain side effects that are unlikely to occur with the consumption of Phenacetin. The filtered and weighted list of side effects is then ready to be visualized for a user under request using a suitable user interface, displaying the drug with the weighted signals.

The precision of the method of invention embodiments can be measured in the following ways:

1. Discarding already known side effects (present in, the knowledge base) for a drug; performing the described method to extract signals for side effects and comparing both lists to measure the ratio of recovered side effects.
2. Taking into consideration available labels in side effects, indicating when a side effect was discovered in a post-market stage or when it was discovered in a pre-market stage; discarding post-market side effects, precision can be measured on the basis of detecting the post-market data.

The low-cost method for early stage signalling of drug side effects described in the present invention permits different users to assess the hypotheses regarding the possible association of side effects to drugs.

As stated previously, embodiments of the present invention try to overcome the drawbacks of the prior art through a method that meets one or more of the following criteria.

A. Is an early detection method that utilizes the data at hand prior to market release, making use of publicly available data from trustworthy sources such as, for example, DrugBank, Sider, and Diseasome at lower cost.

B. Exploits low-cost data usage by utilising open access data and not relying on or requiring patient data and/or experimental trials. Open data allows the system to work and run the detection of adverse effects prior to market release and without patient data availability constraint.

C. Is capable of operating with incomplete data while allowing for the incremental integration of knowledge acquired through the drug manufacturing process and/or other stakeholders. The methods do not require complete data to run the predictions and, thanks to RDF format, new data can be integrated without any extra cost.

The invention claimed is:

1. A system for calculating similarities between drugs and using the similarities to extrapolate side effects of a specified drug, the system comprising:
a similarity-computation apparatus configured to use open data to compute similarities between drugs, the similarity-computation apparatus comprising:
a memory; and
a first processor coupled to the memory and configured to:
obtain data related to a set of drugs from a plurality of open data sources including a plurality of databases and integrate the data to generate Resource Description Framework (RDF) triples;
store an RDF graph of the RDF triples, the RDF graph being a directed graph in which each edge is an RDF triple with a subject-predicate-object structure and in which each edge starts in a subject node and ends in an object node;
retrieve a list of all the drugs present in the RDF graph and find a set of predicates and objects/subjects of RDF triples in which, for each drug in the list, the drug is a subject or an object respectively;
generate a feature vector from the predicates and objects/subjects representing the features of the drug; and
create a vector space model in which each drug is a dot in an n-dimensional space, where n is a cardinality of the feature vectors, using the similarity of each drug with every other drug in the RDF graph, the similarity being calculated using an intersection of Linked Data of the feature vectors of each pair of the drugs, the vector space model being stored in a similarity database with similarity data being drug-drug distances in the n-dimensional space of the vector space model; and
a side effect determining apparatus configured to extrapolate side effects of a specified drug in a set of drugs from open data related to the set of drugs, the side effect determining apparatus comprising:
a user interface configured to allow a user to specify a drug from the set of drugs; and
a second processor configured to rank neighbours and propagate side effects by:
using the drug similarities to obtain nearest neighbours of the specified drug in terms of the similarities, and the second processor is configured to select k nearest neighbours on the basis of distances within the n-dimensional space of the vector space model;
collecting known side effects from the nearest neighbours;
computing frequencies of features of the nearest neighbours occurring with each side effect and building a normalised histogram of drug features for each side effect;
building a correlation matrix to express correlations between all of the side effects and features of the nearest neighbours; and
using the correlation matrix to determine a weight for each side effect collected from the nearest neighbours, the weights indicating the probability of said side effects occurring with use of the specified drug based on the features of the specified drug, and to rank the side effects collected from the nearest neighbours according to the weights,
wherein the user interface is configured to display the ranked side effects and the weights and combining and ranking the side effects according to their co-occurrence among the neighbours to determine side effects of the specified drug, and
wherein the similarity-computation apparatus uses the open data to compute the similarities between the drugs offline for the vector space model stored in the similarity database that is accessed by the side effect determining apparatus for an online query for the side effects of the specified drug.

2. A system according to claim 1, wherein the first processor is configured to allow integration of new data during runtime, and to add the new data to the RDF graph.

3. A system according to claim 1, wherein the first processor is configured to recognise alternative terms for the same drug and to class all the data associated with the alternative terms together as belonging to the same drug and/or wherein the first processor is configured to use alternative names, synonyms and string distance measures to recognise alternative terms for the same drug.

4. A system according to claim 1, wherein the first processor is configured to link together different instances of the same drug using a unique identifier.

5. A system according to claim 1, wherein the plurality of databases include one or more of: drug property, side effects, drug classification and diseases databases.

6. A system according to claim 1, wherein the intersection of the Linked Data of the feature vectors of each pair of the drugs takes into account a number of intersecting features of the feature vectors, in which the predicate and the subject or object is the same for both drugs.

7. A system according to claim 1, wherein the second processor is configured to compute the frequency of drug features occurring with each side effect found among the known side effects to build a correlation between each side effect and each drug feature.

8. A system according to claim 7, wherein the drug features include any one or more of: drug properties, drug classification and diseases.

9. A system according to claim 1, wherein the second processor is configured to issue a warning, alarm or notification with a list of side effects and/or if certain side effects are extrapolated.

10. A method of calculating similarities between drugs and using the similarities to extrapolate side effects of a specified drug, the method comprising:
using open data to compute similarities between drugs, including:
obtaining data related to a set of drugs from a plurality of open data sources including a plurality of databases;
integrating the data to generate Resource Description Framework (RDF) triples;
storing an RDF graph of the RDF triples, the RDF graph being a directed graph in which each edge is an RDF triple with a subject-predicate-object structure and in which each edge starts in a subject node and ends in an object node;
retrieving a list of all the drugs present in the RDF graph and finding a set of predicates and objects/subjects of RDF triples in which, for each drug in the list, the drug is a subject or an object respectively;
generating a feature vector from the predicates and objects/subjects representing the features of the drug; and
creating a vector space model in which each drug is a dot in an n-dimensional space, where n is a cardinality of the feature vectors, using the similarity of each drug with every other drug in the RDF graph, the similarity being calculated using an intersection of Linked Data of the feature vectors of each pair of the drugs, the vector space model being stored in a similarity database with similarity data being drug-drug distances in the n-dimensional space of the vector space model; and
using the similarities to extrapolate side effects of a specified drug, including:
allowing user input specifying a drug from the set of drugs;
obtaining nearest neighbours of the specified drug in terms of the similarities using the similarity database, by selecting k nearest neighbours on the basis of distances within the n-dimensional space;
collecting known side effects from the nearest neighbours;
computing frequencies of features of the nearest neighbours occurring with each side effect and building a normalised histogram of drug features for each side effect;
building a correlation matrix to express correlations between all of the side effects and features of the nearest neighbours; and
using the correlation matrix to determine a weight for each side effect collected from the nearest neighbours, the weights indicating the probability of said side effects occurring with use of the specified drug based on the features of the specified drug, and to rank the side effects collected from the nearest neighbours according to the weights,
wherein the use of the open data to compute the similarities between drugs is performed offline for the vector space model stored in the similarity database that is accessed by the use of the similarities to extrapolate the side effects of the specified drug for an online query for the side effects of the specified drug.

* * * * *